US008728984B2

(12) United States Patent
Oberbauer et al.

(10) Patent No.: US 8,728,984 B2
(45) Date of Patent: May 20, 2014

(54) ACUTE KIDNEY INJURY RISK TESTING

(75) Inventors: Rainer Oberbauer, Vienna (AT); Julia Wilflingseder, Weibern (AT); Bernd Mayer, Vienna (AT); Paul Perco, Vienna (AT); Alexander Kainz, Vienna (AT)

(73) Assignee: Rainer Oberbauer, Vienna (AT)

( * ) Notice: Subject to any disclaimer, the term of this patent is extended or adjusted under 35 U.S.C. 154(b) by 0 days.

(21) Appl. No.: 13/501,665

(22) PCT Filed: Oct. 8, 2010

(86) PCT No.: PCT/EP2010/065118
§ 371 (c)(1),
(2), (4) Date: Apr. 12, 2012

(87) PCT Pub. No.: WO2011/045244
PCT Pub. Date: Apr. 21, 2011

(65) Prior Publication Data
US 2012/0202705 A1    Aug. 9, 2012

(30) Foreign Application Priority Data
Oct. 14, 2009  (EP) .................... 09173058

(51) Int. Cl.
*C40B 40/10*    (2006.01)
(52) U.S. Cl.
USPC .......................................... 506/18
(58) Field of Classification Search
None
See application file for complete search history.

(56) References Cited

U.S. PATENT DOCUMENTS

| | | | |
|---|---|---|---|
| 4,235,960 A | 11/1980 | Sasse et al. | |
| 4,642,285 A | 2/1987 | Halbert et al. | |
| 7,541,160 B2 | 6/2009 | Fei et al. | |
| 2007/0099209 A1* | 5/2007 | Clarke et al. | 435/6 |
| 2008/0161321 A1 | 7/2008 | Feldman et al. | |

FOREIGN PATENT DOCUMENTS

| | | |
|---|---|---|
| WO | WO 00/64873 | 11/2000 |
| WO | WO 2007013919 | 2/2007 |
| WO | WO 2008017306 | 2/2008 |

OTHER PUBLICATIONS

Kehoe B et al., "Elevated Plasma Renin Activity Associated With Renal Dysfunction" Nephron (1986) 44:51-57.
Mydlik M et al., "Plasma Renin Activity and Plasma Aldosterone in Acute Renal Failure," International Urology and Nephrology (1980) 12:83-90.
Perco p. et al., "Protein biomarkers associated with acute renal failure and chronic kidney disease," European Journal of Clinical Investigation (2006) 36:753-763.
Trichet B et al., "Effect of high dose d-1 propranolol on the renin-angiotensin system in glycerol induced acute renal failure in rat," Biomedicine (1978) 28:347-353.
Partial European Search Report, European Patent Application No. 09173058.0, Mar. 18, 2010.
Extended European Search Report, European Patent Application No. 09173058.0, Jun. 9, 2010.
International Search Report, International Patent Application No. PCT/EP2010/065118, Feb. 3, 2010.
International Search Report, International Patent Application No. PCT/EP2010/065118, Nov. 29, 2010.
International Written Opinion, International Patent Application No. PCT/EP2010/065118, Feb. 3, 2010.
International Preliminary Report on Patentability, International Patent Application No. PCT/EP2010/065118, Apr. 17, 2012.

* cited by examiner

*Primary Examiner* — Tracy Vivlemore
*Assistant Examiner* — Karen S Weiler
(74) *Attorney, Agent, or Firm* — Michael Fedrick; Loza & Loza, LLP

(57) ABSTRACT

The present invention relates to the method of determining the risk of acute kidney injury comprising determining the amount of one or more marker(s) selected from REN, SLC38A4, IL17RB, TMEM149, FLRT3, and CATSPERG or any combination thereof in a sample.

5 Claims, No Drawings

ACUTE KIDNEY INJURY RISK TESTING

This application is the U.S. national stage of International Patent Application No. PCT/EP2010/065118, filed on Oct. 8, 2010 and entitled ACUTE KIDNEY INJURY RISK TESTING, which claims the benefit of priority from European Patent Application No. 09173058.0, filed Oct. 14, 2009. The disclosures of the foregoing applications are incorporated herein by reference in their entirety.

The present invention relates to a method for detection, diagnosis, prognosis, or monitoring the risk of acute kidney injury (AKI) by measuring a panel of markers. In particular, the invention refers to a predisposition testing.

AKI is in the clinical setting described as acute renal failure (ARF) or acute tubular necrosis (ATN) and refers to the spontaneous and significant decrease in renal function. AKI therefore reflects the entire spectrum of ARF, recognizing that an acute decline in kidney function is often secondary to an injury that causes functional or structural changes in the kidneys. ARF is a frequent and serious problem with a variety of adverse short- and long-term clinical consequences. Loss of function of the kidney, a vital organ, in the form of acute renal failure represents a special hazard, in particular to older patients, despite modern therapies including the use of the various forms of artificial kidney. In diagnosis and prognosis care must be taken to differentiate between functional renal insufficiency and intrinsic injury with morphologic damage.

AKI in particular in the intensive care unit is often associated with multiple organ failure and sepsis. Furthermore, AKI is associated with high mortality and morbidity in humans. Patients, for instance, experience AKI in ischemic reperfusion injury, along with treatment with nephrotoxic compounds including but not limited to antibiotics or anticancer drugs, application of contrast media e.g. when performing angiography resulting in nephropathy or nephrotoxicity, or at the intensive care unit, e.g. in the context of sepsis. The annual number of patients receiving contrast media is more than 100 million in the developed countries, and the rate of acute kidney injury ranges in a percent range, if coupled to risk factors like hypotension or diabetes.

AKI is usually categorised according to pre-renal, intrinsic and post-renal causes.

Pre-renal (causes in the blood supply):
hypovolemia (decreased blood volume), usually from shock or dehydration and fluid loss or excessive diuretics use.
hepatorenal syndrome, in which renal perfusion is compromised in liver failure
vascular problems, such as atheroembolic disease and renal vein thrombosis (which can occur as a complication of the nephrotic syndrome)
infection usually sepsis, systemic inflammation due to infection
severe burns
sequestration due to pericarditis and pancreatitis
hypotension due to antihypertensives and vasodilators
Intrinsic (damage to the kidney itself):
toxins or medication (e.g. some NSAIDs, aminoglycoside antibiotics, iodinated contrast, lithium, phosphate nephropathy due to bowel preparation for colonoscopy with sodium phosphates)
rhabdomyolysis (breakdown of muscle tissue)—the resultant release of myoglobin in the blood affects the kidney; it can be caused by injury (especially crush injury and extensive blunt trauma), statins, stimulants and some other drugs
hemolysis (breakdown of red blood cells)—the hemoglobin damages the tubules; it may be caused by various conditions such as sickle-cell disease, and lupus erythematosus
multiple myeloma, either due to hypercalcemia or "cast nephropathy" (multiple myeloma can also cause chronic renal failure by a different mechanism)
acute glomerulonephritis which may be due to a variety of causes, such as anti glomerular basement membrane disease/Goodpasture's syndrome, Wegener's granulomatosis or acute lupus nephritis with systemic lupus erythematosus
Post-renal (obstructive causes in the urinary tract) due to:
medication interfering with normal bladder emptying (e.g. anticholinergics).
benign prostatic hypertrophy or prostate cancer.
kidney stones.
due to abdominal malignancy (e.g. ovarian cancer, colorectal cancer).
obstructed urinary catheter.
drugs that can cause crystalluria and drugs that can lead to myoglobinuria and cystitis According to the state of the art, renal failure is diagnosed when either creatinine or blood urea nitrogen tests are markedly elevated in an ill patient, especially when oliguria is present. Previous measurements of renal function may offer comparison, which is especially important if a patient is known to have chronic renal failure as well. If the cause is not apparent, a large amount of blood tests and examination of a urine specimen is typically performed to elucidate the cause of acute renal failure, medical ultrasonography of the renal tract is essential to rule out obstruction of the urinary tract.

An exemplary consensus criterium for the diagnosis of AKI is at least one of the following:
Risk: serum creatinine increased 1.5 times or urine production of less than 0.5 ml/kg body weight for 6 hours
Injury: creatinine 2.0 times OR urine production less than 0.5 ml/kg for 12 h
Failure: creatinine 3.0 times OR creatinine more than 355 μmol/l (with a rise of more than 44) or urine output below 0.3 ml/kg for 24 h
Loss: persistent AKI or complete loss of kidney function for more than four weeks
End-stage Renal Disease: complete loss of kidney function for more than three months.

A rapid increase in serum creatinine may also be an indicator for a high AKI risk following medical treatment, e.g. an impairment in renal function is indicated by an increase in serum creatinine by more than 0.5 mg/dl or more than 25% within 3 days after medication.

Kidney biopsy may be performed in the setting of acute renal failure, to provide a definitive diagnosis and sometimes an idea of the prognosis, unless the cause is clear and appropriate screening investigations are reassuringly negative.

To diagnose AKI, usually urine and blood tests are done and the volume of urine produced is monitored.

The gold standard for diagnosing AKI is the measurement of serum creatinine. Unfortunately, creatinine as marker has several limitations. On the one hand, levels of serum creatinine widely vary among individuals depending on age, sex, muscle mass or medication status. On the other hand, serum creatinine does not accurately depict kidney function during acute changes in glomerular filtration as it is a marker, which can only be interpreted in steady state. Furthermore creatinine levels do not rise until damage is severe and kidney function already declines. Other biomarkers such as lipocalin 2 (LCN2), also known as NGAL (neutrophil gelatinase-associated lipocalin), kidney injury molecule 1 (KIM1), cysteine-rich angiogenic inducer 61 (CYR61), or interleukin 18 (IL18) have recently been proposed as alternative parameters for the detection of acute kidney injury.

WO2008/017306A1 describes a diagnostic test to exclude significant renal injury by measuring neutrophil gelatinase-associated lipocalin (NGAL).

WO2007/013919A2 describes human Gro-alpha as a marker of acute kidney injury.

Perco et al (European Journal of Clinical Investigation (2006) 36, 753-763) describe protein biomarkers associated with acute renal failure and chronic kidney disease.

US20040553877 describes a method comprising administering a renin inhibitor for the prevention of, delay progression to or treatment of a condition or disease such as renal failure, diabetes type 2, severe hypertension among others.

WO0064873A1 discloses renin inhibitors that are used for the treatment of diseases which are associated restenosis, glaucoma, cardiac infarct, high blood pressure and end organ damage, e.g. cardiac insufficiency and kidney insufficiency.

Kehoe et al. Nephron 44(1): 51-57 (1986) describe an association of plasma renin activity to renal dysfunction and tubular injury/dysfunction in the prerenal phase of renal failure.

Trichet et al. Biomedicine 28(6): 347-353 (1978) describe the protective effect of propanolol in a model of renal failure. While a high dose of propanolol increases the plasma level of renin, the renal renin concentration remained unchanged.

Mydlik et al. Int Urol Nephrol 12(1): 83-90 (1980) describe the plasma renin activity in patients in the oliguric phase, the polyuric phase and convalescent phase of acute renal failure.

Patients with normal kidney function are currently not tested for any renal disease markers. In the absence of any functional kidney disorder, such as urine volume reduction or creatinine level, it is assumed that there is no risk for developing AKI. However, there are patients, who have the potential to develop AKI upon certain medical treatment, which could be damaging to the kidney function, such as simple radiography using a contrast medium or chemotherapy. Several risk factors for acute renal failure have been identified so far.

High-risk patients are considered those with chronic diseases that can affect the kidneys like diabetes, hypertension and heart disease. Pregnant patients who suffer from eclampsia, a hypertensive condition, also have a high risk for kidney damage.

Some drugs are nephrotoxic, i.e. poisonous to the kidney, and therefore damaging to the kidneys. This includes certain antibiotics like aminoglycosides, anti-inflammatory drugs and the contrast media used in specific X-ray tests of the urinary tract. A need therefore exists for a marker which can be used to specifically and reproducibly detect the presence of, or predisposition to acquiring AKI clinically leading to ARF.

It is the object of the present invention to provide markers to identify patients with early onset of AKI or predisposition for experiencing ARF.

According to the invention there is provided a method of determining the risk of acute kidney injury in a patient, by determining one or more kidney risk factors (KRF) in a sample from said patient, which KRF is selected from the group consisting of renin (REN), solute carrier family 38, member 4 (SLC38A4), interleukin 17 receptor B (IL17RB), transmembrane protein 149 (TMEM149), fibronectin leucine rich transmembrane protein 3 (FLRT3), and the cation channel, sperm-associated, gamma (CATSPERG). The determination of the risk of AKI also includes the determination of the AKI predisposition, diagnosis and prognosis of developing AKI or ARF, respectively. Thus, it is understood that an individual at risk of AKI also has a predisposition, diagnosis and prognosis of developing AKI and/or ARF. In particular, the risk of genuine AKI is determined according to the invention. It is understood that the diagnostic method according to the invention commonly is employing ex vivo, in particular in vitro testing.

Preferably the method according to the invention comprises determining the level of said KRF, which is at least 1.2 times increased, preferably at least 1.5 times increased, compared to a control. In a method according to the invention, which employs the determination of at least two of said KRF, the preferred level of each KRF is at least 1.2 times increased, preferably at least 1.5 times increased, compared to a control, to distinguish patients at risk of AKI.

The KRFs according to the invention are highly predictive of AKI, reaching area under the ROC curve of at least 0.8 using the Summer's D statistic. Thereby it is possible to determine the AKI risk in a reliable way.

Though it is possible to determine the KRF according to the invention, which is membrane bound, it is preferred to determine the soluble KRF, or the soluble and/or plasma membrane bound KRF, as a marker of the AKI risk.

In a preferred embodiment the expression of KRF is determined in said sample, such as the polypeptide or polynucleotide level of said KRF.

The preferred method according to the invention employs a sample, which is selected from the group consisting of tissue or physiological fluids, such as blood, serum, plasma or urine sample, especially a urine sample. Less preferred, but possible, is the determination of a KRF in an invasive sample, such as a biopsy sample. Further preferred samples are obtained from tissues, extracts, cell cultures, cell lysates and lavage fluid.

The condition, which can be detected with the inventive methods is in particular a patient at risk of developing AKI, which can e.g. be determined by using a kidney biopsy sample and also by detecting the markers in serum, blood, plasma or urine by comparing reference values of non-progressive renal disease values or from healthy subjects.

Preferably the method according to the invention is applied to a patient, who is suffering from a chronic disease, such as metabolic disease, diabetes, hypertension or heart disease.

In another preferred embodiment the patient is tested for the risk status according to the invention before receiving potentially nephrotoxic medication.

According to a preferred method, the KRF is determined by microarray hybridization with specific probes or by PCR.

In another aspect, the invention refers to a panel of markers for determining acute renal failure or the AKI risk, consisting of at least two markers selected from the group consisting of REN, SLC38A4, IL17RB, TMEM149, FLRT3, and CATSPERG. It is therefore contemplated that one or more of said markers are used to manufacture a diagnostic product to determine AKI or the AKI risk.

Thus, a set of reagents for determining the AKI risk is preferably specifically binding to at least two markers of the panel according to the invention.

The preferred set according to the invention comprises reagents, which are ligands specifically binding to said markers.

Preferably the ligands are nucleotide sequence specific oligonucleotides or antibodies or antibody fragments. It is further preferred that the reagents are labelled.

Therefore, the present invention provides a method of detection, diagnosis, prognosis, monitoring or predisposition testing of acute kidney injury by determining the amount of a marker selected from REN, SLC38A4, IL17RB, TMEM149, FLRT3, and CATSPERG or any combination thereof in a sample. For the inventive method, one of these markers can be detected, or a combination of any two, three, four, five, or six of these markers, or any combination with at least one of the markers according to the invention with a further risk factor associated with AKI.

Specifically preferred combination of markers are REN and SLC38A4 as well as REN, IL17RB and FLRT3.

The inventive markers are:

1. REN—Renin (UniGene: Hs.3210, GeneID: 5972, GenBank: AA458630/AA455535): Renin is a highly specific endopeptidase, who's only known function is to generate angiotensin I from angiotensinogen in the plasma, initiating a cascade of reactions that produce an elevation of blood pressure and increased sodium retention by the kidney.

2. SLC38A4—solute carrier family 38, member 4 (UniGene: Hs.446077, GeneID: 55089, GenBank: N68679): SLC38A4 is a sodium-dependent amino acid transporter. It mediates electrogenic symport of neutral amino acids and sodium ions and has a broad specificity, with a preference for Ala, followed by His, Cys, Asn, Ser, Gly, Val, Thr, Gln and Met. SLC38A4 may mediate sodium-independent transport of cationic amino acids, such as Arg and Lys. Amino acid uptake is pH-dependent, with low transport activities at pH 6.5, intermediate at pH 7.0 and highest between pH 7.5 and 8.5.

3. IL17RB-interleukin 17 receptor B (UniGene: Hs.654970, GeneID: 55540, GenBank: H90761): IL17RB is a receptor for the proinflammatory cytokines IL17B and IL17E and may play a role in controlling the growth and/or differentiation of hematopoietic cells.

4. TMEM149—transmembrane protein 149 (UniGene: Hs.352548, GeneID: 79713, GenBank: AA701412).

5. FLRT3—fibronectin leucine rich transmembrane protein 3 (UniGene: Hs.41296, GeneID: 23767, GenBank: AA455382).

6. CATSPERG—cation channel, sperm-associated, gamma (UniGene: Hs.324335, GeneID: 57828, GenBank: AA906919)

These markers, including but not limited to respective polypeptides and nucleotide sequences, such as native-sequence polypeptides, isoforms, chimeric polypeptides, any derivative, part or polymorphism (including without limitation splice variant) of such biomolecules, all homologs, fragments, and precursors of the markers, and modified forms of the polypeptides and derivatives, or nucleic acids encoding such polypeptides, are referred to herein as "Kidney Risk Factors (s)" (KRF) or inventive KRF.

Thus, the present invention provides a panel of markers, also called biomarkers, that can be used in a method for detection, diagnosis, prognosis, or monitoring the acute kidney injury (AKI), including the risk for experiencing acute renal failure (ARF) In particular, the inventive method allows the determination of the predisposition for developing AKI or respective risk stages, e.g. to distinguish between low, medium and high risk patients.

The term "panel" as used herein shall refer to a predetermined group of markers that are subject to medical tests as a tool in the diagnosis and treatment of disease. Panels (sometimes called profiles) as used herein are typically composed of individual laboratory tests which are related in some way: by the medical condition they are intended to help diagnose (AKI Risk Panel). The diagnostic test panel according to the invention offers various advantages over individual diagnostic tests to laboratories performing the tests (labor efficiency, potential for automation and reduced costs through performing large numbers of the same kinds of tests each day), as well as to end users such as ordering physicians and hospitals (more comprehensive testing, rapid turn-around and lower prices). The presence of several tests responsive to the same clinical condition may also increase the chances of detecting that condition. The term shall specifically refer to the reference material including or consisting of the selected markers, e.g. for use as controls, qualitative or quantitative references.

In a specific embodiment, the invention contemplates marker sets containing or consisting essentially of at least two, three, four, five or six KRF, wherein at least one of the KRFs is selected from the inventive panel, preferably at least two, three, four, five or six of the KRFs according to the invention. The marker sets are preferably polypeptide or genetic marker sets representing the KRF or respective binders, e.g. comprising a plurality of respective polypeptides, genes or polynucleotides.

KRF are thus preferably determined by testing for KRF polypeptides and KRF polynucleotides. In the following, KRF determination always refers to the detection and/or testing for one or more KRF polypeptides or KRF polynucleotides. KRF determination is specifically proposed in the method according to the invention for determining the risk for developing an acute kidney disease or an acute kidney disorder, and in particular in the detection of the risk of developing AKI within a short, medium or long-term period, depending on medical treatment and care. Besides determining the predisposition or risk status of a patient, the markers can be used for diagnosis, monitoring, i.e. monitoring progression or therapeutic treatment, prognosis, treatment, or classification of respective kidney disease, or as markers before or after therapy.

Preferably those patients are tested for KRF with normal kidney function, where no kidney disease is diagnosed by standard means. Normal kidney function is defined as a glomerular filtration rate above 70 ml/min, preferably above 80 ml/min, more preferably above 90 ml/min and essentially no proteinuria. Other endocrine functions are of no relevance in this proposal and thus not discussed here.

The identification of a patient's risk or predisposition is essential in the patient population that is already classified as high-risk patients. It is thus preferred to test a patient population according to the invention, which is already classified as risk patients, for instance, patients with risk factors of age, preexisting chronic illness, malnutrition, cancer, severe trauma, or sepsis. In particular, it is indicated to test patients suffering from metabolic disease, such as diabetic disease, hypertension or heart or vascular disease, Typically, patients suffering from AKI are not tested for the AKI risk according to the invention.

The inventive method can also include the step of obtaining the sample from a patient at risk for developing acute kidney injury, e.g. before contrast medium administration in the course of angiography. Thus, the term "patients" herein always includes healthy subjects. The subject can, e.g., be any mammal, in particular a human, but also selected from mouse, rat, hamster, cat, dog, horse, cow, pig, etc.

Reference values for the KRF are preferably obtained from a control group of patients or subjects with normal expression of said KRF, or a KRF expression, that is afflicted with kidney stress conditions, such as septic, cancer or diabetic patients, without proteinuremia or AKI, which represents the appropriate reference patient group. In a particular aspect, the control comprises material derived from a pool of samples from normal patients.

Thus, the method according to the invention is specifically provided for determining susceptibility to kidney disease, such as AKI, by determining a KRF in a patient comprising:

(a) obtaining a sample from a patient, (b) detecting or identifying in the sample a KRF, and (c) comparing the detected amount with an amount detected for a reference.

The term "detect" or "detecting" includes assaying, imaging or otherwise establishing the presence or absence of the target KRF encoding the markers, subunits thereof, or combinations of reagent bound targets, and the like, or assaying for, imaging, ascertaining, establishing, or otherwise determining one or more factual characteristics of kidney disease or similar conditions. The term encompasses diagnostic, prognostic, and monitoring applications for a KRF.

The invention also provides a method of assessing whether a patient is at risk of AKI, comprising comparing:

(a) levels of a KRF in a sample from said patient, and (b) normal levels of a KRF in samples of the same type obtained from control patients, wherein altered levels of the KRF relative to the corresponding normal levels is an indication that the patient has an AKI risk, e.g. a predisposition to kidney disease, such as AKI, in particular where detection of a level of KRF that differs significantly from the standard indicates acute kidney disease or onset of kidney disease or increased risk for developing ARF. A significant difference between the levels of a KRF in a patient and the normal levels is an indication that the patient has a risk of kidney disease or a predisposition to kidney disease, such as AKI.

In a preferred embodiment, the method according to the invention for assessing whether a patient has a risk of kidney disease or a pre-disposition for kidney disease, higher levels of KRF in a sample relative to the corresponding normal levels is an indication that the patient has kidney disease or a pre-disposition for kidney disease.

The risk of acute kidney injury is indicated if the amount of a marker or the combination of markers is increased at least 1.2 times the reference value of subjects not suffering from AKI, preferably being subjects from a control group or healthy subjects. Usually an increase below a 1.5 fold increase of an individual marker reflects a relatively low risk; at least 1.5 fold, but below 2.0 fold increase is considered a medium risk; at least 2.0 fold increase would indicate a high-risk. If at least two KRFs are increased, the risk is considered to be increased as well. Thus, at least 1.2-1.4 fold increase of each of at least two KRFs already determines the medium to high-risk stages.

For the purpose of the AKI risk determination, in special embodiments the amount of any one of the inventive KRF is at least 1.2, preferably at least 1.4, at least 1.8, at least 2, or at least 3 times the reference value, in particular as determined by microarray analysis.

If more than one marker is detected, the comparison is made to each single reference value for each marker in the reference itself. The inventive prognosis method can predict whether a patient is at risk of developing acute kidney injury. The higher the fold increase, the higher is the patient's risk of AKI. An elevated KRF indicates, for example, special treatment of the patient, using appropriate medication or contrast media. The method of the invention can thus be used to evaluate a patient before, during, and after medical treatment.

Likewise, the KRF level can be compared to a cut-off concentration and the kidney disease development potential is determined from the comparison; wherein concentrations of KRF above the reference concentrations are predictive of, e.g., correlate with, kidney disease development in the patient.

Thus, the preferred method according to the invention comprises the step of comparing the KRF level with a predetermined standard or cut-off value, which is preferably at least 50% higher than the standard, more preferred at least 60% or 70% higher, but can also be at least 100% higher.

In aspects of the methods of the invention, the methods are non-invasive for AKI predisposition testing, which in turn allow for diagnosis of a variety of conditions or diseases associated with acute kidney disease. In particular, the invention provides a non-invasive non-surgical method for detection, diagnosis, monitoring, or prediction of acute kidney disease or onset of kidney disease in a patient comprising: obtaining a sample of blood, plasma, serum, urine or saliva or a tissue sample from the patient; subjecting the sample to a procedure to detect one or more KRF by comparing the levels of KRF to the levels of KRF obtained from a control.

The invention also contemplates a method of assessing the potential of a test compound to contribute to kidney disease or onset of kidney disease comprising:

(a) maintaining separate aliquots of a sample from a patient in the presence and absence of the test compound, and (b) determining and comparing the levels of one or more of KRF in each of the aliquots.

This is particularly useful in monitoring the KRF level in clinical trials. A significant difference between the levels of a KRF in an aliquot maintained in the presence of or exposed to the test compound relative to the aliquot maintained in the absence of the test compound, indicates that the test compound potentially contributes to kidney disease or onset of kidney disease.

Likewise, the invention according to the invention can be employed to determine the effect of an environmental factor on kidney disease comprising comparing one or more KRF associated with kidney disease or onset of kidney disease in the presence and absence of the environmental factor.

The inventive markers, sometimes called biomarkers, can be detected in any sample of a subject comprising said markers e.g. where an expression of a KRF is determined either as polynucleotide, e.g. as mRNA, or expressed polypeptide or protein. The comparison with the reference value should be of the same sample type.

When a marker panel is used for the AKI risk determination, it is preferred that the inventive KRFs are determined either as membrane bound markers and/or soluble markers. Thus, a panel of reagents is preferably selected that allows for the determination of the same sample and KRF expression type.

In preferred embodiments, determining the amount of the marker or any combination thereof comprises determining the expression of the marker(s), preferably by determining the mRNA concentration of the marker(s). To this extent, mRNA of the sample can be isolated, if necessary, after adequate sample preparation steps, e.g. tissue homogenisation, and hybridized with marker specific probes, in particular on a microarray platform with or without amplification, or primers for PCR-based detection methods, e.g. PCR extension labelling with probes specific for a portion of the marker mRNA. In preferred embodiments the marker(s) or a combination thereof is (are) determined by microarray hybridization with REN, SLC38A4, IL17RB, TMEM149, FLRT3, CATSPERG specific probes or by PCR.

Differential expression of the polynucleotides is preferably determined by micro-array, hybridization or by amplification of the extracted polynucleotides. The invention contemplates a gene expression profile comprising one or more of the KRF that is associated with AKI predisposition. This profile provides a highly sensitive and specific test with both high positive and negative predictive values permitting diagnosis and prediction of the patient's risk of developing disease.

For example, the invention provides a method for determining the AKI risk in a patient comprising (a) contacting a sample obtained from said patient with oligonucleotides that hybridize to a KRF, and (b) detecting in the sample a level of polynucleotides that hybridize to the KRF relative to a predetermined reference or cut-off value, and therefrom determining the AKI risk in the subject.

Within certain preferred embodiments, the amount of polynucleotides, e.g. mRNA, are detected via polymerase chain reaction using, for example, oligonucleotide primers that hybridize to a KRF, or complements of such polynucleotides. Within other embodiments, the amount of mRNA is detected using a hybridization technique, employing oligonucleotide probes that hybridize to a KRF, or complements thereof. When using mRNA detection, the method may be carried out by combining isolated mRNA with reagents to convert to cDNA according to standard methods and analyzing the products to detect the presence of KRF in the sample.

In particular aspects of the invention, the methods described herein utilize one or more KRF placed on a microarray so that the expression status of each of the markers is assessed simultaneously. In an embodiment, the invention provides a microarray comprising a defined set of KRF genes, whose expression is significantly altered by an AKI risk. The invention further relates to the use of the microarray as a prognostic tool to predict kidney disease.

In further embodiments the amount of a marker or any combination thereof is determined by the polypeptide or protein concentration of the marker(s), e.g. with marker specific ligands, such as antibodies or specific binding partners. The binding event can, e.g., be detected by competitive or non-competitive methods, including the use of labelled ligand or marker specific moieties, e.g. antibodies, or labelled competitive moieties, including a labelled marker standard, which compete with marker proteins for the binding event. If the marker specific ligand is capable of forming a complex with the marker, the complex formation indicates expression of the markers in the sample.

In particular, the invention relates to a method for diagnosing and monitoring acute kidney disease in a patient by quantitating a KRF in a biological sample from the subject comprising (a) reacting the biological sample with one or more binding agents specific for the KRF, e.g. an antibody that is directly or indirectly labelled with a detectable substance, and (b) detecting the detectable substance.

KRF levels can be determined by constructing an antibody microarray, in which binding sites comprise immobilized, preferably monoclonal antibodies specific to a marker. The invention also relates to kits for carrying out the methods of the invention.

The invention further contemplates the methods, compositions, and kits described herein using additional markers associated with kidney disease. The methods described herein may be modified by including reagents to detect the additional markers, or polynucleotides for the markers.

Appropriate probes, specific antibodies or methods for determining the inventive KRFs are well-known in the art.

Monoclonal antibodies for detection of renin (REN) are for example available from Abcam plc, Cambridge, UK, under the product names "Renin antibody [BGN/09/2028]" and "Renin antibody [BGN/09/2076]".

Antibodies for detection of interleukin 17 receptor beta (IL17RB) are available from Abnova Corporation (Taiwan) (Catalog Number H00055540-A01) or Lifespan Biosciences (Seattle, Wash., USA) (Catalog ID LS-C70963).

Antibodies for detection of transmembrane protein 149 (TMEM149) are available from Abcam plc. (Product name TMEM149 antibody) or Lifespan Biosciences (Catalog ID LS-C81473).

Antibodies for detection of solute carrier family 38 member 4 (SLC38A4) are available from Aviva Systems Biology Aviva Systems Biology LLC (San Diego, Calif., USA) (Catalog Number ARP42504_T100) or Abcam plc. (Product name SLC38A4 antibody).

Antibodies for detection of fibronectin leucine rich transmembrane protein 3 (FLRT3) are available from Lifespan Biosciences (Catalog ID LS-C36368) or R & D Systems (Catalog ID BAF2795).

The I.M.A.G.E clones (http://image.hudsonalpha.org/) for detection of mRNAs via hybridization experiments for the 6 KRF are IMAGE:813402 for REN, IMAGE:293240 for SLC38A4, IMAGE:240506 for IL17RB, IMAGE:435894 for TMEM149, IMAGE:812143 for FLRT3, and IMAGE: 1503670 for CATSPERG.

In general, immunoassays involve contacting a sample containing or suspected of containing a marker of interest with at least one antibody that specifically binds to the marker. A signal is then generated indicative of the presence or amount of complexes formed by the binding of polypeptides in the sample to the antibody. The signal is then related to the presence or amount of the marker in the sample. Numerous methods and devices are well known to the skilled artisan for the detection and analysis of markers. See, e.g., U.S. Pat. Nos. 4,235,960; 4,642,285; 7,541,160. The Immunoassay Handbook, David Wild, ed. Stockton Press, New York, 1994, each of which is hereby incorporated by reference in its entirety, including all tables, figures and claims.

The assay devices and methods known in the art can utilize labelled molecules in various sandwich, competitive, or non-competitive assay formats, to generate a signal that is related to the presence or amount of the marker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labelled molecule. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In exemplary embodiments, the analyte is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

In a further aspect the present invention provides a set of at least two different marker specific moieties, each specific for a KRF to determine at least two KRFs, wherein at least one of the KRFs is selected from the panel according to the invention, e.g. more than two, three, four, five or six marker specific moieties, wherein at least two or more, such as three, four, five or six markers selected from REN, SLC38A4, IL17RB, TMEM149, FLRT3, or CATSPERG can be determined.

As a read out, the amount of parameters in a sample to determine the inventive KRF may be measured and correlated to the risk of said patients, which can be low, medium or high, or else prediction rules established in order to discriminate between the binary outcome AKI or not. For example, the ability of a prediction rule can be assessed by calculating the area under the ROC curve (AUC) using the Sommer's D statistic. The relation between the area under the ROC and Sommer's D is the following:

$$AUC=(1+\text{Sommer's }D)/2.$$

It is preferred to employ a KRF according to the invention either as single predictor of progression or as marker combinations, with an AUC value of at least 0.8, preferably at least 0.85, more preferred 0.9, 0.95 or even up to 1.0.

Preferred marker combinations can be derived from the examples and Table 2 below, which are reaching area under the curve (AUC) values of at least 0.8, preferably at least 0.85, more preferred at least 0.9, 0.95 or up to 1.0. Likewise, any combination of at least one KRF of the panel according to the invention with another KRF, which brings about an AUC value as described above, is considered a preferred combination to determine the AKI risk.

Marker specific moieties are substances which can bind to or detect at least one of the markers for a detection method described above and are in particular marker nucleotide sequence detecting tools or marker protein specific antibodies, including antibody fragments, such as Fab, F(ab), F(ab)', Fv, scFv, or single chain antibodies. The marker specific moieties can also be selected from marker nucleotide sequence specific oligonucleotides, which specifically bind to a portion of the marker sequences, e.g. mRNA or cDNA, or are complementary to such a portion in the sense or complementary anti-sense, like cDNA complementary strand, orientation.

For easy detection the moieties are preferably labelled, such as by optical, including fluorescence, and radioactive labels.

The present invention is further illustrated by the following examples without being limited thereto.

EXAMPLES

Example 1

Patient Samples

Human renal biopsies of kidney transplant donors were collected. 10 kidney biopsies were included for cDNA microarray analysis. Donor kidney biopsies were examined pre-transplantation by a pathologist and the degree of glomerulosclerosis (gs), arteriolosclerosis (as), interstitial fibrosis (if), interstitial inflammation (ii), tubular atrophy (tc) as well as acute tubulus damage (ta) was assessed following a semi-quantitative grading system: 0—no; 1—minor; 2—moderate; 3—severe damage. Based on the histological parameter of acute tubulus damage (ta) two groups were defined, namely those samples showing no or only minor tubulus damage (n=6) and the other group of samples with moderate or severe tubulus damage (n=4). Acute tubular damage is a histological parameter strongly correlated to acute kidney injury and thus was used to identify marker candidates separating samples with no or only mild damage versus samples with moderate to severe tubulus damage. Microarray-based gene expression profiling was performed in those 10 patients' samples.

Example 2

RNA Isolation and Microarray Hybridization

Sample preparation followed established experimental steps as described previously (Hauser et al. Lab Invest 2004, Kainz et al. Am J Transpl 2004). All organs were perfused with a histidine-tryptophan-ketoglutarat (HTK) cold preservation solution at 4° C. during organ procurement. Wedge biopsy of each kidney was performed under sterile conditions at the end of the cold ischemic time right before transplantation. The biopsy specimens were immediately submerged in RNAlater™ (Ambion, Austin, Tex.) and stored at 4° C. for not longer than five days.

Total RNA was isolated and purified using chloroform and trizol reagent (Invitrogen, Carlsbad, Calif.), and the RNA yield and quality was checked with the Agilent 2100 Bioanalyzer and RNA6000 LabChip® kit (Agilent, Palo Alto, Calif.). Stratagene Universal human reference RNA was used as reference (Stratagene, La Jolla, Calif.).

Two micrograms of isolated total RNA were amplified using the RiboAmp RNA amplification kit (Arcturus, Mountain View, Calif.). The amplified RNA was inspected on an ethidium bromide stained 1% agarose gel and on the Agilent 2100 Bioanalyzer.

cDNA microarrays holding 41,409 features were obtained from the Stanford University Functional Genomics core facility (batch No.: sheo). A type II experimental setup was used, where each of the samples was hybridized along with a common reference to a microarray. Stratagene Universal human reference RNA, composed of total RNA from 10 human cell lines, served as reference. One microgram of sample and standard Stratagene Universal human reference RNA were labeled with CyScribe cDNA post labeling kit (Amersham Pharmacia Biotech, Buckinghamshire, UK) in a two-step procedure. Samples were loaded onto arrays and incubated for 16 hr in a water bath at 65° C. After three washing steps, the fluorescence images of the hybridized microarrays were examined using a GenePix 4100A scanner (Axon Instruments, Union City, Calif.). The GenePix Pro 4.1 software was used to grid images and to calculate spot intensities. The arrays were numbered according to the anonymous organ donor ID and were processed in random order.

Example 3

Statistical Analysis and Selection of Putative Biomarkers

Signals showing intensity signal over background values lower than 1.5 in either channel were excluded and the analyses were focused on genes with valid data in at least 75% of processed samples in each of the two groups under study, leaving 16221 cDNA clones in the analysis dataset. A two-sample t-test (p<0.05) and the two-fold-change criterion were used to identify differentially expressed genes (DEGs) when comparing samples with no or only mild tubular damage to those samples with moderate to severe tubular damage.

The subcellular location of DEGs was determined using data stored in the SwissProt database as well as bioinformatics prediction routines based on the protein sequence, and special emphasis was laid on proteins located in the plasma membrane.

Example 4

Microarray Analysis 18 differentially expressed transcripts mapping to 11 unique annotated genes upregulated in the samples with moderate to severe acute tubular damage could be identified. Six of these identified genes had protein isoforms which were located in the plasma membrane according to information stored in the SwissProt database as well as bioinformatics prediction routines based on the protein sequence. These genes are renin (REN), solute carrier family 38, member 4 (SLC38A4), interleukin 17 receptor B (IL17RB), transmembrane protein 149 (TMEM149), fibronectin leucine rich transmembrane protein 3 (FLRT3), and the cation channel, sperm-associated, gamma (CATSPERG).

TABLE 1

Results

| GeneName | GeneSymbol | p-value | Fold-change (array) |
|---|---|---|---|
| renin | REN | 0.034 | 3.48 |
| solute carrier family 38, member 4 | SLC38A4 | 0.048 | 2.89 |
| interleukin 17 receptor B | IL17RB | 0.033 | 2.81 |
| transmembrane protein 149 | TMEM149 | 0.040 | 2.69 |
| fibronectin leucine rich transmembrane protein 3 | FLRT3 | 0.014 | 2.19 |
| cation channel, sperm-associated, gamma | CATSPERG | 0.025 | 2.13 |

Example 5

P-Values for Specific Combinations

Based on gene expression data of the six KRFs under study we established prediction rules in order to discriminate between the binary outcome acute tubular damage (moderate to severe) or no acute tubular damage (none to mild damage). We assessed the ability of the prediction rule by calculating the area under the ROC curve (AUC) using the Sommer's D statistic. The relation between the area under the ROC and Sommer's D is AUC=(1+Sommer's D)/2. AUC values of 1.0 indicate complete discrimination of the two groups based on the marker values, whereas values of 0.5 indicate random assignment.

In this study the best single predictor with an AUC value of 1 is SLC38A4 as well as FLRT3, followed by IL17RB (AUC=0.944), REN (AUC=0.933) as well as CATSPERG (AUC=0.933), and TMEM149 (AUC=0.867). Preferred marker combinations reaching AUC values greater than 0.9 are exemplarily REN and SLC38A4 as well as REN, IL17RB and FLRT3. A complete listing of AUC values of the respective markers and marker combinations based on gene expression data is given in the table below.

TABLE 2

Results

| Number | Model | AUC |
|---|---|---|
| 1 | REN | 0.93333 |
| 2 | SLC38A4 | 1 |
| 3 | IL17RB | 0.94444 |
| 4 | TMEM149 | 0.86667 |
| 5 | FLRT3 | 1 |
| 6 | CATSPERG | 0.93333 |
| 7 | REN SLC38A4 | 1 |
| 8 | REN IL17RB | 1 |
| 9 | REN TMEM149 | 1 |
| 10 | REN FLRT3 | 1 |
| 11 | REN CATSPERG | 1 |
| 12 | SLC38A4 IL17RB | 1 |
| 13 | SLC38A4 TMEM149 | 1 |
| 14 | SLC38A4 FLRT3 | 1 |
| 15 | SLC38A4 CATSPERG | 1 |
| 16 | IL17RB TMEM149 | 0.93333 |
| 17 | IL17RB FLRT3 | 1 |

TABLE 2-continued

Results

| Number | Model | AUC |
|---|---|---|
| 18 | IL17RB CATSPERG | 0.93333 |
| 19 | TMEM149 FLRT3 | 1 |
| 20 | TMEM149 CATSPERG | 0.93333 |
| 21 | FLRT3 CATSPERG | 1 |
| 22 | REN SLC38A4 IL17RB | 1 |
| 23 | REN SLC38A4 TMEM149 | 1 |
| 24 | REN SLC38A4 FLRT3 | 1 |
| 25 | REN SLC38A4 CATSPERG | 1 |
| 26 | REN IL17RB TMEM149 | 1 |
| 27 | REN IL17RB FLRT3 | 1 |
| 28 | REN IL17RB CATSPERG | 1 |
| 29 | REN TMEM149 FLRT3 | 1 |
| 30 | REN TMEM149 CATSPERG | 1 |
| 31 | REN FLRT3 CATSPERG | 1 |
| 32 | SLC38A4 IL17RB TMEM149 | 1 |
| 33 | SLC38A4 IL17RB FLRT3 | 1 |
| 34 | SLC38A4 IL17RB CATSPERG | 1 |
| 35 | SLC38A4 TMEM149 FLRT3 | 1 |
| 36 | SLC38A4 TMEM149 CATSPERG | 0.93333 |
| 37 | SLC38A4 FLRT3 CATSPERG | 1 |
| 38 | IL17RB TMEM149 FLRT3 | 1 |
| 39 | IL17RB TMEM149 CATSPERG | 0.93333 |
| 40 | IL17RB FLRT3 CATSPERG | 1 |
| 41 | TMEM149 FLRT3 CATSPERG | 1 |
| 42 | REN SLC38A4 IL17RB TMEM149 | 1 |
| 43 | REN SLC38A4 IL17RB FLRT3 | 1 |
| 44 | REN SLC38A4 IL17RB CATSPERG | 1 |
| 45 | REN SLC38A4 TMEM149 FLRT3 | 1 |
| 46 | REN SLC38A4 TMEM149 CATSPERG | 0.93333 |
| 47 | REN SLC38A4 FLRT3 CATSPERG | 1 |
| 48 | REN IL17RB TMEM149 FLRT3 | 1 |
| 49 | REN IL17RB TMEM149 CATSPERG | 1 |
| 50 | REN IL17RB FLRT3 CATSPERG | 1 |
| 51 | REN TMEM149 FLRT3 CATSPERG | 1 |
| 52 | SLC38A4 IL17RB TMEM149 FLRT3 | 1 |
| 53 | SLC38A4 IL17RB TMEM149 CATSPERG | 1 |
| 54 | SLC38A4 IL17RB FLRT3 CATSPERG | 1 |
| 55 | SLC38A4 TMEM149 FLRT3 CATSPERG | 1 |
| 56 | IL17RB TMEM149 FLRT3 CATSPERG | 1 |
| 57 | REN SLC38A4 IL17RB TMEM149 FLRT3 | 1 |
| 58 | REN SLC38A4 IL17RB TMEM149 CATSPERG | 1 |
| 59 | REN SLC38A4 IL17RB FLRT3 CATSPERG | 1 |
| 60 | REN SLC38A4 TMEM149 FLRT3 CATSPERG | 1 |
| 61 | REN IL17RB TMEM149 FLRT3 CATSPERG | 1 |
| 62 | SLC38A4 IL17RB TMEM149 FLRT3 CATSPERG | 1 |
| 63 | REN SLC38A4 IL17RB TMEM149 FLRT3 CATSPERG | 1 |

Example 6

AKI Risk Assessment

In the following example the difference of diagnosing acute kidney injury and prognosing acute kidney injury (AKI) to happen in the near future can be demonstrated.

Sera protein concentrations exemplarily for a kidney risk factor is determined in patients receiving contrast medium before angiography. The KRF concentration is determined in serum before contrast medium administration and the concentration is correlated with the renal status after contrast medium treatment expressed as creatinine values.

Sample Collection:

Sera samples are collected from patients before receiving contrast medium. Patients older than 18 years undergoing peripheral/coronary angiography and/or computer tomography (CT) with normal kidney function before receiving contrast medium (defined as serum creatinine (SCr)<1.5 mg/dl) are included in the study. Two vials of 5 ml blood each are collected from each patient before receiving contrast medium by venipuncture on the patient's forearm. Blood is processed following standard procedures; serum is labelled uniquely and stored at −80° C. At the same time serum creatinine is determined from a separate vial.

After a median of 24 hours after receiving contrast medium, blood is drawn again as described above. Two 5 ml vials are used for the serum repository; a third vial is used for determining the serum creatinine after contrast medium treatment.

Patient core data (patient code, date of birth, gender) as well as clinical parameters (serum creatinine, hemoglobin, LDH) are collected and managed in a fully anonymous, multi-centric patient data acquisition and management system.

Acute kidney injury (AKI) is defined as rise in serum creatinine values as determined after contrast medium administration of at least 0.3 mg/dl and more than 25% of the serum creatinine value as determined before contrast medium administration.

For those patients showing AKI based on the definition given above, serum before administration of contrast medium is selected for determining the KRF concentration.

A corresponding reference cohort of patients with no acute kidney injury (non AKI) is determined by caliper matching. Matching is performed for the following four variables:

Creatinine values before contrast medium administration
Patient age
Diabetes mellitus yes/no
Volume of contrast medium administered Methods:

ELISA kits, are used to determine the KRF protein concentration in the patient samples The ELISA experiments are performed following the manufacturer's protocol for ELISA processing.

A significant positive correlation of KRF concentration before contrast medium administration and the change in serum creatinine values (given in %) can be observed.

Sera KRF concentration are higher in the samples of patients who experienced AKI after contrast medium treatment when compared to patients who did not experience AKI after treatment with contrast medium.

This example may illustrate the difference between AKI diagnosis and AKI risk assessment: At the time point of measuring the risk assessment marker no acute kidney injury is diagnosed as creatinine levels are in a normal range. However, a risk assessment marker, KRF, is already elevated and this elevation provides information on an increased likelihood for experiencing AKI in the future.

The invention claimed is:

1. A set of reagents for determining acute renal failure, wherein the reagents specifically bind to at least two markers selected from the group consisting of REN, SLC38A4, IL17RB, TMEM149, FLRT3, and CATSPERG, wherein at least one of the markers is selected from the group consisting of CATSPERG, SLC38A4, and TMEM149.

2. The set of reagents of claim 1, wherein said reagents are labelled.

3. The set of reagents of claim 1, wherein the reagents include SLC38A4.

4. The set of reagents of claim 1, wherein the reagents include CATSPERG.

5. The set of reagents of claim 1, wherein the reagents include TMEM149.

* * * * *